United States Patent [19]

Sanderson

[11] Patent Number: 4,722,948

[45] Date of Patent: Feb. 2, 1988

[54] BONE REPLACEMENT AND REPAIR PUTTY MATERIAL FROM UNSATURATED POLYESTER RESIN AND VINYL PYRROLIDONE

[75] Inventor: John E. Sanderson, North Miami, Fla.

[73] Assignee: Dynatech Corporation, Cambridge, Mass.

[21] Appl. No.: 829,281

[22] Filed: Feb. 13, 1986

Related U.S. Application Data

[63] Continuation-in-part of Ser. No. 590,169, Mar. 16, 1984, abandoned.

[51] Int. Cl.$^4$ .............................................. A61F 2/00
[52] U.S. Cl. .................................... 523/115; 523/113; 523/114; 523/526; 525/445; 525/447
[58] Field of Search ............... 523/115, 113, 114, 526; 525/445, 447

[56] References Cited

U.S. PATENT DOCUMENTS 3,107,427  10/1963  Schmitt et al. ...................... 525/447

*Primary Examiner*—Harold D. Anderson
*Attorney, Agent, or Firm*—Cesari and McKenna

[57] ABSTRACT

A bone replacement and repair material prepared from a biocompatible polyester resin, a liquid linking agent capable of cross-linking the resin and a filler is moldable and formable and cures in vivo. The resulting cured putty also degrades in vivo to provide interstices in the polyester matrix for new tissue growth. The polyester resin can also be used as an implantable matrix containing a pharmaceutical agent therein for sustained release of said pharmaceutical from said matrix in a physiological environment.

16 Claims, 1 Drawing Figure

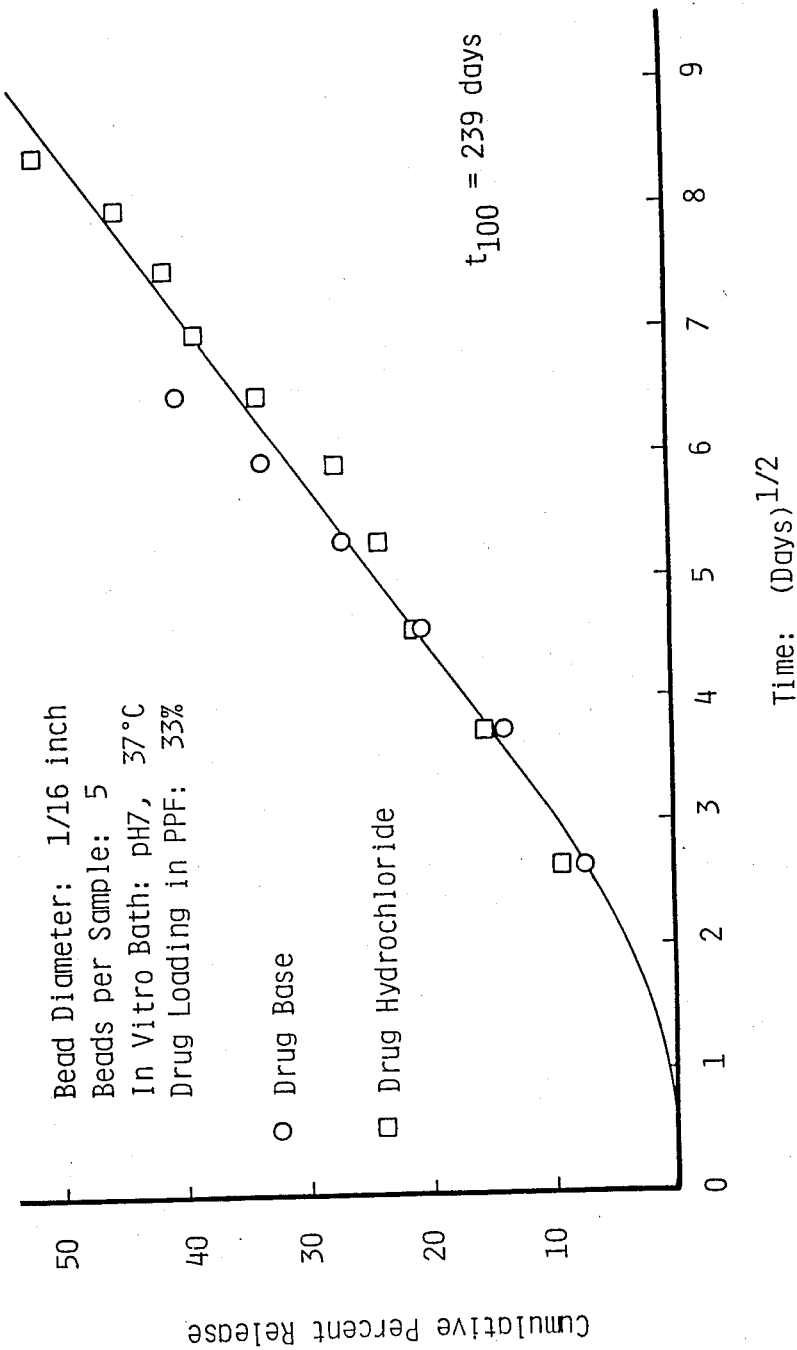

BONE REPLACEMENT AND REPAIR PUTTY MATERIAL FROM UNSATURATED POLYESTER RESIN AND VINYL PYRROLIDONE

CROSS REFERENCE TO RELATED APPLICATIONS

This application is a continuation-in-part application of U.S. application Ser. No. 590,169, filed Mar. 16, 1984, now abandoned.

FIELD OF THE INVENTION

This invention discloses useful medical and veterinary applications of a polyester composed of biocompatible acids and an alcohol. This invention relates to bone replacement and repair materials, and more specifically to moldable, biodegradable, synthetic biocompatible materials curable at physiologic temperatures. The invention also relates to biodegradable synthetic materials suitable for implantation for the delivery of pharmaceutical agents.

BACKGROUND OF THE INVENTION

The technology of bone replacement and repair has been the focus of considerable medical and scientific research, and has broad application in the treatment of a variety of bone disorders. For example, one application lies in repair of injuries which destroy skeletal segments or leave substantial gaps between these segments. Of particular importance is the repair of avulsive maxillofacial wounds. Of great utility to an orthopedic surgeon in repairing such injuries is a moldable or otherwise readily conformable material which can be used to fill cavities and openings between adjacent or formerly connected portions of bone, immobilizing the entire bone structure of concern. Injuries of the kind described are encountered frequently as a consequence of military combat. In these military applications, the repair materials must be easily manipulated at the surgical site and they must meet the special logistical demands of military utilization when only temporary emergency medical facilities are available. In all such surgical procedures, it is desirable that they produce esthetically acceptable results.

Another application is in treatment of periodontal disease, caused by bacterial erosion of the connective tissue between the gums and the teeth. One current treatment involves opening and cleaning the infected periodontal cavity, treating the cavity with antibiotics and packing it with crushed bone. This procedure apparently aids in the reconstruction of the support tissue for the tooth. However, it is difficult to apply and pack loose crushed bone into the eroded areas of the gums, and a more suitable application process would be advantageous.

Other potential bone repair applications involve supplying internal support to weakened and brittle bones of patients with osteoporosis or osteosarcoma, and the resurfacing of joints affected by arthritis. Another potential application for bone repair material is in the preparation of pre-molded plates, pins, and screws for orthopedic mending of bone parts.

Among substances which have been used as cements or to replace missing bone sections are polymers and copolymers of lactic and glycolic acids, polyethylene oxide/polyethylene terephthalate copolymers, polymethylmethacrylate, and higher homologs of the alpha-alkyl-cyanoacrylates. Pre-formed ceramic materials filled with calcium phosphate have also been investigated for use in bone repair. Methyl methacrylate has been used in applications such as bonding artificial hip joints to the femur. Ideally, a bone replacement and repair material should be biocompatible, formable in situ to a desired size and shape, and biodegradable while promoting or allowing natural bone ingrowth for ultimate repair of the injury. Preformed materials lack the flexibility required to accomodate odd-shaped and sized bone injuries, and must be bonded to natural bone by a cement. Also, methyl methacrylate cement, while formable to some extent, is composed of toxic methacrylate monomer, and requires special handling. Furthermore, it is not biodegradable and the heat generated by the curing of the cement may raise the temperature of surrounding tissues above 56° C. This temperature will kill adjacent bone tissue.

SUMMARY OF THE INVENTION

Accordingly, the present invention aims to provide an improved synthetic bone replacement and repair material and method for making same that is moldable and formable to a desired configuration so that it can fill cracks and voids, replace missing bone fragments, and reinforce degraded bone.

It is a further object of the present invention to provide a bone replacement and repair material that is curable at physiologic temperatures.

Another object of the present invention is to provide a moldable bone replacement and repair material that is curable to a rigid structure that has adequate mechanical strength to substitute for the missing bone it replaces.

Still another object of the present invention is to provide a bone replacement and repair material that is biocompatible with tissue.

Still another object of the present invention is to provide a bone replacement and repair material that is biodegradable and develops porosity to enable intrusion of new bone tissue.

Still another object is to provide a kit for preparing a bone replacement and repair material.

Still another object of the invention is to provide a biodegradable, implantable material for release of a designated pharmaceutical agent therefrom.

Other objects will, in part be obvious, and will in part appear hereinafter.

Briefly, my repair material is based on the use of biocompatible, biodegradable polymers, synthesized from substances naturally occurring in the body or acceptable therein, that are readily metabolized or degraded to an excretable form. Naturally occurring substances are found in the Krebs cycle, or tri-carboxylic acid cycle, of metabolism, as described in U.S. Pat. No. 3,978,203. For example, a polymer prepared by a reaction between fumaric acid, a Krebs cycle acid, and a physiologically tolerable alcohol, such as propylene glycol, produces a suitable polyester resin that can be cross-linked to produce a rigid structure and yet is biodegradable in vivo. However, experiments have shown that the polymers themselves do not cross-link to form a rigid structure upon addition of an initiator, unless either high temperatures (110° C.) or lengthy times (22 hours) are employed. To increase the rate of cross-linking between polymer chains at physiological temperatures, a diffusable, biocompatible linking agent, e.g.

vinyl pyrrolidone, is used to link the polymer chains together to form the desired rigid structure.

Preferably, the repair material also contains a filler which, together with the polymer and linking agent, produces a workable, moldable paste or putty of the uncured material, capable of retaining shape while being formed. The putty can then be cured to a rigid structure by addition of the initiator, which subsequently causes the linking agent to react with the polymer chains. The resulting repair material is biodegradable, formable, and curable at physiologic temperatures within a short time.

In summary, the repair material comprises an unsaturated polyester resin, a linking agent, filler, and an initiator, all of which are biocompatible. A typical formulation contains 20 parts filler, 8 parts polyester, 3 parts linking agent, and 0.25 parts initiator.

The material is prepared in two parts. A first part is prepared from filler, polyester, and one-half to three-quarters of the linking agent. This mixture forms to a taffy-like consistency and is capable of retaining its shape and structure. A second part comprises an initiator dissolved in the remainder of the linking agent, so as to be miscible with the first part. When the first and the second parts are mixed together, the resulting combination is a moldable, formable putty that retains its plasticity for fifteen to thirty minutes. It ultimately cures to a rigid structure that retains the quality of biodegradability.

It has also been found that matrices prepared from one of the above polyesters, poly-(propylene fumarate), can be shaped into an implant for use in delivering a pharmaceutical agent from the matrix.

DETAILED DESCRIPTION OF THE PREFERRED EMBODIMENTS

The foregoing and other features of the invention will be more readily understood from the following detailed description, when taken in conjunction with the accompanying drawing, in which FIG. 1. is a graphical presentation of experiments showing drug release from matrices of poly-(propylene fumarate), prepared according to the methods described below.

The following working examples are given as illustrative embodiments of the products and processes for producing them. Numerous variations of these examples can be effected without departing from the invention.

PART I. PREPARATION OF POLYMER

Poly-(propylene fumarate) is synthesized from diethyl fumarate and propylene glycol by transesterification using para-toluenesulfonic acid as a catalyst. A one liter round-bottom flask is fitted with a 25 cm Vigreaux column and standard distilling head. A typical equimolar reaction mixture of 344 g diethyl fumarate, 152 g propylene glycol, and 1 g para-tolunesulfonic acid is added to the flask. The temperature of the mixture is slowly raised over the period of reaction to an end point of 240° C.–250° C. by steady application of heat through the bottom of the flask by a fitted electric heating mantle.

A distillate begins to evolve at a temperature of 78° C. measured at the top of the Vigreaux column, above the reaction mixture. This temperature continues essentially throughout the balance of the reaction period, indicating that the distillate is ethanol, the expected product of the condensation reaction between diethyl fumarate and propylene glycol. The reaction is allowed to proceed for approximately five hours, or until the temperature in the reaction mixture reaches 250° C. and no more distillate can be collected. At this point, approximately 175 ml of distillate has been removed.

The reaction mixture is then cooled to below 100° C. and the Vigreaux column is removed. A vacuum pump is attached to the system to remove remaining volatile components. The reaction mixture is then reheated to 220° C. under a vacuum of approximately 1 mm Hg for a period of approximately four hours. At this time, an additional 75 ml distillate has been collected.

After cooling under continuous evacuation, the reaction mixture, a clear, thick, viscous mass, is dissolved in approximately 200 ml methylene chloride. A high-molecular weight polymer of poly-(propylene fumarate) can then be separated by fractional precipitation with ether. Specifically, the dissolved reaction mixture is transferred dropwise to an open vessel containing anhydrous ether (approximately 5 volumes ether to one volume of methylene chloride) with constant agitation until the mixture becomes cloudy, indicating that the polymer is precipitating. To ensure that the maximum proportion of the polymer product is precipitated, additional ether is added at this point. The resulting suspension and precipitate in ether is refrigerated to a temperature of $-20°$ C. and the supernatant liquid is decanted. The residue is then washed twice with 50 ml fresh ethyl ether. The washed precipitate is placed in a vacuum dessicator and dried under vacuum at room temperature for 48 hr to yield a white to yellow or yellow-amber powder. The powder has a softening temperature of about 80° C. The yield of the final product was about 35 percent determined by final weight of the polymer compared with the weight of initial reaction mixture less the weight of the distillate collected.

Similar polymers can be prepared from other Krebs cycle acids. For example, as described in U.S. Pat. No. 3,978,203, polymers can be prepared from reactions between other di- and tri-carboxylic acids found in the Krebs cycle with biologically compatible alcohols, such as glycerol, mannitol, and sorbitol. Examples of these include citric, cis-aconitic, isocitric, a-ketoglutaric, succinic, malic, and oxaloacetic acids. The Krebs cycle acids may be in the form of an anhydride, a diacid chloride, or a salt. It may also be in the form of a methyl or ethyl derivative.

Also, copolymers containing two of the Krebs cycle acids can be prepared. For example, fumaric acid contains an unsaturated bond, and is therefore, capable of cross-linking, whereas succinic acid lacks this point of unsaturation. A copolymer containing both fumaric and succinic acids may provide more controlled cross-linking of the polymer and produce a structure in which the molecular distance between successive cross-links may be greater than that obtained with a polymer prepared from fumaric acid alone.

Therefore, in a preferred embodiment of the present invention I have provided a moldable, biodegradeable putty that cures at physiological temperatures, said putty comprising a mixture of:

A. An unsaturated polyester resin formed as a reaction product of one or more biocompatible acids, at least one of which is an unsaturated acid, and an alcohol. The unsaturated acid can be fumaric acid or cis-aconitic acid, or an anhydride, acid chloride, salt, or methyl or ethyl derivative of such an acid. The biocompatible acids can be fumaric acid, citric acid, malic acid, cis-acontitic acid, isocitric acid, alpha-ketoglutaric acid, succinic acid, or oxaloacetic acid, or an anhydride, acid chloride, salt, or methyl or ethyl derivative of such an acid. The alcohol can be glycerol, mannitol, sorbitol or propylene glycol;

B. Vinyl pyrrolidone;
C. A filler; and
D. A free radical initiator for initiating cross-linking of the polyester resin with the vinyl pyrrolidone.

PHYSICAL PROPERTIES OF THE POLYMER

In the working example, poly-(propylene fumarate) was characterized by viscosity measurements and by gel permeation chromatography. The average molecular weight distribution was determined by Gel Permeation Chromatography of a solution of polymer in tetrahydrofuran using a Waters Micro Styrogel column. It was estimated from chromatography profiles that the preparative procedure yields material of molecular weight 90% within the range 1300–124,000 Daltons.

DEGRADABILITY OF POLYMER

The polymer formed by the above process was tested for susceptibility to hydrolytic degradation. During polymer formation, some cross-linking of the linear chains occurs, which prevents complete hydrolysis, and hence, complete degradability of the polymer. One method to determine whether a polymer is sufficiently cross-linked to prevent degradation is to test hydrolizability in 1 N NaOH solution. Dissolution of the sample as soon as heating has begun suggests that the sample will be ultimately biodegradable at neutral pH and body temperatures. Polymer prepared according to the methods described above was completely dissolved by warm 1 N NaOH.

PART II. PREPARATION OF A MOLDABLE, CURABLE PUTTY

The following is an example of a process of making the putty according to the invention.

A moldable, curable putty is prepared in two parts, A and B. Part A of a typical formulation comprises 12 g CaSO$_4$.2H$_2$O filler, 4 g poly-(propylene fumarate) prepared as described in Part I of the process, and 1 g N-vinyl-2-pyrrolidone. The vinyl pyrrolidone acts as solvent for a portion of the dry polymer. The balance of polymer and calcium sulfate in this mixture is dispersed and suspended. The mixture is formed by kneading and working the ingredients, as the high proportion of dry polymer and filler are not readily blended into the vinyl pyrrolidone. The resultant mixture has a taffy-like consistency.

Part B of the formulation comprises 0.12 g benzoyl peroxide, a free radical initiator used to initiate cross-linking, that is dissolved in 0.5 g N-vinyl-2-pyrrolidone.

When Parts A and B are mixed together, the combination containing the enhanced proportion of fluid becomes a moldable, putty-like mixture which remains plastic for fifteen to thirty minutes, and then cures to a rigid structure.

A kit can be prepared with two compartments, one containing Part A, with the ingredients described above, and the other containing the ingredients of Part B as described above. The Parts A and B may also be prepared as described above and packaged separately. The two parts are then mixed together shortly before the putty is to be used.

The putty can contain up to seventy percent by weight of filler. Fillers can be inorganic materials such as calcium phosphate, calcium carbonate, or hydroxyapatite. They can also be powdered polymers such as polylactic acid, poly-(propylene fumarate), or other biocompatible polymers that are ultimately eliminated from the body. Powdered biological substances such as crushed bone, or demineralized bone particles also are suitable filler materials. For use as a bone replacement and repair material, calcium phosphate, crushed bone, or demineralized bone particles are preferred.

IN VITRO TESTS ON CURED PUTTY

1. The cured putty, prepared as described above, was tested for hardness and compressibility, to determine whether it has properties consistent for use as a substitute for bone. The putty was prepared and formed into a 0.4 inch diameter cylindrical mold, and allowed to cure at 37° C. Sixteen hours later, the resulting rod was removed from the mold and cut into one-half inch segments using a hacksaw. The ends of each piece were squared on a lathe using a facing tool. Each segment was measured for hardness using a Shore D-2 hardness tester. The average hardness was found to be 84±2.3, equivalent to about 98 Rockwell C.

The same samples were tested to determine the compression strength of the cured putty. An Instron tester was used with a crosshead speed of 0.1 inch per minute. Results showed a compressibility equivalent to about 50 MPa. While this compressive strength is slightly less that that recommended for methacrylate bone cements, it is adequate for a temporary application such as maxilofacial injury repair. Furthermore, the strength of the cured putty can be increased by increasing the molecular weight of the polymer or by changing the ratio of polymer to filler.

2. The cured putty was tested for loss of filler under physiological conditions. Leaching of the filler should occur at a relatively uniform, slow rate to provide space for nascent bone ingrowth. Optimally, the putty should secure bone fragments together, promote bone ingrowth into the putty-filled area, and be replaced by the new bone.

Beads 1.5 mm in diameter were transfer molded from a putty prepared according to the methods described above and cured at 37° C. Five such beads were weighed and suspended in test tubes with 50 ml distilled water. The tubes were placed in a shaker bath at 37° C., and gently agitated for sixteen days. The beads were removed, dried, and weighed. A weight loss of 50% was detected. The beads did, however, maintain their structural integrity. Presumably, therefore, the weight loss was due primarily to leaching of the calcium sulfate filler. These results suggest that when the material is implanted into an internal physiological environment, the filler will leach out into the surrounding tissues, thereby providing interstices in the polymeric matrix for new tissue growth.

3 Putty, prepared according to the methods, was cured in an aqueous environment to determine whether it retained its consistency prior to curing. These experiments were performed to ascertain the suitability for modelling an oral implant, which is subjected to an aqueous environment. Samples of putty, approximately ten grams in weight, were prepared and placed in a beaker of saline solution at 37° C. The samples remained intact and cured to rigid structures within less than thirty minutes.

IN VIVO TESTS

1. In vivo tests of the putty for use as a bone replacement material were performed in rats. Bone putty was prepared according to the methods, except that powdered human bone was used as filler, instead of calcium sulfate, as shown in the methods. One-eighth inch holes were drilled in the cranium and tibia in four rats, and plugs of bone putty, prepared just prior to implantation, were packed into the drilled openings in three of the rats and allowed to cure therein. The fourth rat was kept without putty filling as a control.

The rats were maintained for four to six weeks, sacrificed, and the drilled/filled areas were inspected by skilled personnel. The bone had grown together in the control animal. In the experimental animals, the bone had also grown together and some residual putty was observed in the drilled/filled areas. When these sections of the bone were removed and analyzed more closely, it was determined that bone tissue had grown into the putty-plugs. These results indicate that the plugs degraded in vivo in the rats and allowed for new bone growth into interstices in the plugs.

It is believed that with some fillers, the bone regrowth into the pores resulting from removal of filler from the putty involves the process termed osteoconduction. On the other hand, when demineralized bone is used as the filler for a porous and/or biodegradable matrix of cross-linked poly-(propylene fumarate) or homologous polymer, it is believed that the bone regrowth involves an alternate process of osteoinduction. In that process, mesenchymal tissue is converted first into a cartiliginous structure and finally into new bone. Since osteoinduction may occur throughout the mass of an implant carrying demineralized bone particles, the healing or bridging of gaps between bone ends may be more rapid than the process of osteoconduction, in which new bone grows only from the margin of the old bone tissue into the framework of a biodegradable matrix.

2. Experiments were initiated to evaluate the use of the putty described above, in treatment of periodontal disease. In four dogs, one-eighth inch diameter holes were drilled in a tooth near or below the gum line. Putty was prepared as described in the methods, except that powdered human bone was used as a filler. The drilled holes were packed with the putty, to mimic the situation where periodontal cavities are filled. The putty was allowed to cure to a rigid structure. This experience indicates that moldable putty prepared according to the methods can be used to place treatment agents in periodontal cavities. Previous procedures to place unconsolidated powdered bone in the periodontal cavity were unsatisfactory.

PART III. PREPARATION OF IMPLANTABLE SUSTAINED RELEASE DRUG DELIVERY SYSTEMS

The description following reveals how the polymer poly-(propylene fumarate) may be utilized to formulate a composition suitable for implantation within the body and having the useful function of delivering a medicament or other active agent to the host tissues.

The following example describes how to prepare poly(propylene fumarate) for such uses. The following ingredients were charged to a three-neck glass reaction flask:

| Ingredients | grams | g. moles |
| --- | --- | --- |
| Diethyl fumarate | 34.21 | 0.2 |
| Propylene glycol | 15.2 | 0.2 |
| Paratoluene sulfonic acid | 0.1 | |
| Tert-butyl hydroquinone | 0.08 | |
| Silicone Oil, DC 200 50 cs | 100 ml | |

The flask was fitted with a magnetic stirring device and placed inside an air convection oven. Connection was made from the flask to a water-cooled reflux condenser followed by a condensation trap cooled by dry ice in methanol and connected to a vacuum pump. The temperature of the oven was raised to 175° C. and maintained within the range 175°–180° C. for 48¼ hours while the pressure in the reaction flask was allowed to remain at atmospheric. The pressure was then reduced to 20 mm Hg and maintained for an additional 110 hours while the temperature in the flask was about 165° C.

The silicone oil was poured off and the polymer residue washed with hexane. The polymer was then dissolved in 50 mls of methanol and cooled to −17° C. in a 38×200 mm test tube. A dark, viscous polymer layer collected in the lower part of the test tube. The light brown supernatant layer was poured off and 100 ml of ethyl ether was added. The mixture was warmed to 32° C., stirred thoroughly and then cooled to room temperature and the supernatant layer discarded. 100 ml of a 50/50 mixture of methanol and ether was then added, mixed, allowed to settle and the supernatant discarded. Addition of 100 ml of ether precipitated polymer as a solid on the sides of the test tube. The supernatant liquor was discarded. The resulting polymer is hereinafter designated as polymer-I, or poly-(propylene fumarate)-I. Polymer-I was then dissolved in 25 ml of methanol and 25 ml of methylene chloride containing 0.005 g of tert-butyl hydroquinone. After removal of the solvents under vacuum, 5.46 g of a brittle yellow brown resin was obtained (yield 8.8% of theoretical). This resin softened at about 80° C. and pulled out into long strings when molten. It will be seen that, while the proportions of the polymer-I constituents, diethyl fumarate, propylene glycol, and para-toluene sulfonic acid, are virtually identical to those described above in the Preparation of the Polymer, the polymer-I was prepared in the presence of an anti-oxidant, tert-butyl hydroquinone, and in a suspension of silicone oil.

Analysis of the polymer-I by gel permeation chromatography showed it to have a number average molecular weight of about 20,000. The polymer-I was used in the preparation of an injectable, powder dose form, designated as dose form I. Such a powder is made injectable through an ordinary hypodermic need by suspending the powder form in an aqueous medium, e.g. 1% carboxy methyl cellulose. The injections are made either subcutaneously or intramuscularly.

The injectable, powdered sustained release dose form I was prepared with the poly-(propylene fumarate)-I described above as matrix material and the antipsychotic, sedative drug, thioridazine (10-[(1-methyl-2-piperidyl)ethyl]-2-(methylthio)phenothiazine) hydrochloride. Two grams of thioridazine hydrochloride manufactured by Sandoz, Incorporated, and 4 grams of poly-(propylene fumarate)-I were dissolved in 35 milliliters of methylene chloride. The solution was spread out as a film in a Pyrex pie plate, and air dried. The dry film was then scraped as a coarse powder from the pie plate and vacuum dried overnight at 60° C. The dry powder was then extruded under pressure through a 1/16" diameter die at 70° to 71° C. 5.3 grams of light brown shiny rod were obtained.

The rod was subjected to grinding to produce a fine powder. The powder was sieved and the matter in the particle size range 90 to 180 microns was segregated for test and evaluation.

In another preparation of poly-(propylene fumarate), hereinafter designated as poly-(propylene fumarate)-II or polymer-II, four times the quantity of reactants described above for the preparation of polymer-I, were suspended in 350 ml silicone oil in a 1000 ml three-necked flask arranged as described before. Reaction was permitted to proceed 90 hours at 760 mm Hg followed by 309 hours at 20 mm Hg. After reaction for 148 hours at 2.00 mm Hg, 0.03 grams of tert-butyl hydroquinone antioxidant was added to the mixture.

The crude polymer-II was washed with hexane and dissolved in 100 ml of anhydrous methanol. After cooling to −17° C., the supernatant methanol was discarded, the polymer-II was warmed to 32° C. and dissolved in 50 ml ether with a thorough stirring. The mixture was cooled to −17° C. and the supernatant liquid discarded. Adding 200 ml of methanol and 100 ml of a 50/50 mixture of methanol and ether with constant stirring precipitated some of the polymer-II as a cream colored powder. The mixture was then cooled to −17° C. and the liquid portion decanted. Next 300 ml of ether were added, the mixture was again stirred well and the ether decanted. The purified polymer-II was dissolved in a minimum amount of a 50/50 mixture of methanol and methylene chloride containing 0.03 g of tert-butyl hydroquinone antioxidant. The color of the solution was dark brown. Analysis by gel permeation chromatography showed the polymer to have a number average molecular weight of 17,000. This polymer was used to prepare an implantable bead dose form, designated as bead dose form II, containing either thioridazine hydrochloride or thioridazine base.

Thioridazine base was prepared by dissolving 6.7 grams of the hydrochloride in 100 ml of distilled water and 23 ml of 1N NaOH added. A sticky precipitate formed. After decanting the water, the sticky material was dissolved in a minimum quantity of warm acetone. The crystals formed at −17° C. even though most of the acetone had evaporated leaving a viscous liquid. After the addition of more acetone and seeding with a few crystals of the hydrochloride form of the drug, a quantity of crystals formed. After filtration, washing with a minimum quantity of cold acetone (−17° C.), and drying, the melting point of the crystals obtained was determined to be 72°–74° C., the value for thioridazine base. (The melting point of thioridazine hydrochloride crystals is 158°–160° C.)

Two bead dose forms II were prepared, one with thioridazine hydrochloride, and one with thioridazine base. In order to prepare these bead dose forms II, approximately 4 grams of poly-(propylene fumarate)-II and approximately 2 grams of thioridazine powder, either hydrochloride or base form was dissolved in 25 ml methylene chloride. The solution was filtered through a Millipore screen to remove any foreign particles present. The filtered solution was spread out as a film in a clean Pyrex pie plate and air dried. The dry film was then scraped as a coarse powder from the pie plate and vacuum dried overnight at 60° C. Spherical 1/16" diameter beads were then transfer molded from the powder at 75° C. Spectrophotometric analysis showed the two bead preparations to have thioridizine contents of 32.7% (hydrochloride form) and 33.5% (base form), respectively.

It is apparent that other pharmaceuticals may be substituted for thioridizine described in this example. These agents include antibiotics, anti-pain drugs, agents affecting the central nervous system, pharmacodynamic agents, chemotherapeutic agents, anti-neoplastic agents, natural and synthetic hormones, anti-inflammatory agents, agents affecting thrombosis,

PART IV. PERFORMANCE OF SUSTAINED RELEASE DRUG DELIVERY SYSTEMS

Upon implantation of biocompatible, biodegradable, hydrolizable dose forms like those described above into living tissue, the drug content will be delivered to the body of the host. In vitro tests were conducted to demonstrate such a process.

Weighed samples of the dose forms-II, containing thioridazine hydrochloride or thioridazine base were placed in 10×50 mm Whatman extraction thimbles and a plug of glass wool inserted to occlude the entrance of the thimbles. These thimbles were suspended in 200×29 mm borosilicate glass test tubes containing 60 ml of pH 7 buffer solution (Fisher Scientific Co. Catalog No. P2352). These test tubes were held in an oscillating oil bath maintained at 37° C.±0.01° C. for extended periods of time. Periodically aliquot samples of the buffer solution were withdrawn for analysis of thioridazine content for computation of cumulative drug release. Care was taken to replace the buffer solution periodically so that elevated concentrations of extracted thioridazine did not hinder the rate of drug extraction. Account was taken of the drug content of the discarded buffer.

The results of these evaluation tests of the delivery of thioridazine from 1/16" diameter beads of poly-(propylene fumarate) polymer-II containing 33% drug when leached in vitro at 37° C. in pH 7 buffer are summarized in FIG. 1. These data are presented as cumulative quantity of drug released from the beads as a function of the square root of the duration of the test. This method of graphical presentation of the data was chosen to test the supposition that the rate of drug release from these spheres is described mathematically by the relationship $$R = \sqrt{kt} + C,$$

where
R = Percent Drug Release
k = a constant, day$^{-1}$
t = time, days
C = a constant The mathematical justification of this and other drug delivery relationships is discussed by R. Langer, *Chem. Eng. Communications*, Vol. 6, pages 1–48, Gordon and Breach Science Publishers, 1980. It will be seen that the data follow this relationship quite well, encouraging the estimation of the length of time required to exhaust the drug content, i.e., when R = 100%, through the relationship $t(100) = (R-C)^2/k$, to be 239 days.

The surprising result of these tests was the observation that the rate of delivery of the hydrochloride form of thioridazine is virtually identical to that of the base form. The hydrochloride form of the drug is soluble in water, whereas the base form is much less soluble, thus the two drug forms are expected to have significantly different rates of extraction from the polymer matrix by a surrounding aqueous medium. The fact that the extraction rates differ very little suggests that the control of drug release is by erosion of the polymer matrix rather than by permeation of the matrix by fluid and diffusion of the drug to the medium surrounding the beads. This discovery identifies poly-(propylene fumarate) as an erodable matrix system, a useful quality which may provide the formulator of drug release systems with a tool for control of performance not attainable with systems controlled by permeation and diffusion.

In Vitro tests were made of drug delivery for the 90-180 micron injectable powder (form I) prepared as described above using poly-(propylene fumarate)-I containing 33% by weight thioridazine hydrochloride. The drug was delivered more rapidly from the powder than from the beads, for example, 45% extracted in 5 days; 65% in 10 days. The time to extract 100% was estimated to be 26 days, following the mathematical procedure outlined above. This indicates that the extraction from the powder is about 10 times more rapid than from the beads. This is consistent with the ratio of the surface areas of the particles. The surface area of 1/16" (1.6 mm diameter) beads and of a 150 micron diameter (0.15 mm diameter) spherical particles are 8 mm$^2$ and 0.07 mm$^2$, respectively. The respective volumes are 2 mm$^3$ and 0.0018 mm$^3$ so that the surface area of enough 150 particles to have the same volume as one 1/16" diameter bead is (2 $mm^3$/0.0018 $mm^3$)×0.07 $mm^2$=77 mm$^2$ or about 10 times the surface area of one 1/16" diameter bead.

These evaluations indicate that these dose forms would have usefulness in delivering drug from an implant for about one month in the case of the injectable powder (form I) and about 7-8 months in the case of the beads (form II).

SUMMARY

It can be seen from the foregoing description that a moldable putty, prepared according to the methods described above, cures in vivo to a rigid structure at physiological temperatures and at a relatively rapid rate. Furthermore, the cured putty degrades in vivo thereby providing interstices therein for bone ingrowth.

Furthermore, it can be seen that poly-(propylene fumarate) can be used as an implantable matrix containing a pharmaceutical agent for sustained release of the agent therefrom.

It will thus be seen that the objects set forth above, among those made apparent from the preceeding description, are efficiently attained. Also, certain changes may be made in carrying out the above constructions without departing from the scope of the invention.

For example, other biocompatible, reactive linking agents such as diethyl fumarate can be substituted for vinyl pyrrolidone. The initiator, benzoyl peroxide, is soluble in this agent. Other suitable initiators include t-butyl hydroperoxide (Lucidol HEPV251), methyl ethyl ketone peroxide (Lucidol DDM-9), and t-butyl perbenzoate (Lucidol). Moreover, biocompatible accelerators or promoters can be added, as desired.

Therapeutic agents can be added to the putty formulation to enhance selected functions of the putty, and provide new additional functions to it. When the putty is used to replace missing bone fragments, bone growth factors can be mixed therein to promote repair of the affected bone segment by stimulating new bone growth.

In situations where infection is likely, as in military wounds or in periodontal cavities, antibiotics can be added to the putty. The antibiotics will slowly leach out of the putty into the surrounding tissues, just as the fillers have been demonstrated to do, thereby preventing further infection.

Also, components such as anti-oxidants can be added to enhance shelf-life of the putty components. One suitable food-grade anti-oxidant is Tenox (TBHQ).

Demonstration of the behavior of implantable beads and powders was given, but implants having other geometry, e.g. cylinders, shperes, ellipsoids, and other shapes may be used to generate special release profiles.

It will also be apparent that a multiplicity of medicaments or active agents, rather than a single substance alone, may be incorporated in the subject implants for release therefrom.

Accordingly, it is intended that the matter contained in the above descripton and shown in the accompanying figures be interpreted as illustrative and not in a limiting sense.

It is also to be understood that the following claims are intended to cover all the generic and specific features of the invention herein described.

What is claimed as new and desired to be secured by the Letters Patent of the United States is:

1. A moldable, biodegradable putty that cures at physiological temperatures, said putty comprising a mixture of:
    A. an unsaturated polyester resin formed as a reaction product of one or more biocompatible acids, at least one of which is an unsaturated acid, and an alcohol;
        (1) said unsaturated acid selected from a group consisting of fumaric acid, and cis-aconitic acid, or an anhydride, acid chloride, salt or methyl-/ethyl derivative of said acid,
        (2) said biocompatible acids selected from a group consisting of fumaric acid, citric acid, malic acid, cis-aconitic acid, isocitric acid, alpha-ketoglutaric acid, succinic acid, and oxaloacetic acid, or an anhydride, acid chloride, salt or methyl/ethyl derivative of said acid, and
        (3) said alcohol selected from a group consisting of glycerol, mannitol, sorbitol and propylene glycol;
    B. vinyl pyrrolidone;
    C. a filler; and
    D. a free radical initiator for initiating cross-linking of said polyester resin with said vinyl pyrrolidone.

2. A putty according to claim 1 wherein said initiator is selected from a group consisting of benzoyl peroxide, t-butyl hydroperoxide, methyl ethyl ketone peroxide, and t-butyl perbenzoate.

3. A putty according to claim 1 wherein said filler is selected from a group consisting of calcium sulfate, calcium carbonate, calcium phosphate, hydroxyapatite, poly-(lactic acid), crushed bone or particles of demineralized bone.

4. A putty according to claim 1 further including an anti-oxidant to increase shelf-life.

5. A formable, implantable biodegradable putty, curable in situ, said putty prepared by mixing
    A. a pliant taffy comprising:
        (1) poly-(propylene fumarate), dissolved in,
        (2) vinyl pyrrolidone, and (3) a filler; and B. a solution of an initiator dissolved in vinyl pyrrolidone for initiating cross-linking of the dissolved poly-(propylene fumarate) with the vinyl pyrrolidone.

6. A putty according to claim 5 wherein said filler consists essentially of powdered poly-(propylene fumarate).

7. A putty according to claim 5 wherein said initiator is selected from a group consisting of benzoyl peroxide, t-butyl hydroperoxide, methyl ethyl ketone peroxide, and t-butyl perbenzoate.

8. A putty according to claim 5 wherein said filler is selected from a group consisting of calcium sulfate, calcium carbonate, calcium phosphate, hydroxyapatite, powdered poly-(lactic acid), crushed bone or particles of demineralized bone.

9. A formable, implantable, biodegradable putty curable at physiological temperatures and usable as a bone implant, said putty comprising a mixture of:

A. poly-(propylene fumarate),
B. a filler,
C. vinyl pyrrolidone, and
D. an initiator for cross-linking the poly-(propylene fumarate) with the vinyl pyrrolidone.

10. An implantable putty according to claim 9 for use as a bone replacement and repair material.

11. An implantable putty according to claim 9 for use in filling periodontal cavities.

12. A putty according to claim 9 wherein said initiator is selected from a group consisting of benzoyl peroxide, t-butyl hydroperoxide, methyl ethyl ketone peroxide, and t-butyl perbenzoate.

13. A putty according to claim 9 wherein said filler is selected from a group consisting of calcium sulfate, calcium carbonate, calcium phosphate, hydroxyapatite, crushed bone or particles of demineralized bone.

14. A putty according to claim 9 wherein said filler consists essentially of powdered poly-(propylene fumarate) or powdered poly-(lactic acid).

15. A putty according to claim 9 further including an anti-oxidant to increase shelf-life.

16. A kit for providing a moldable, implantable, biodegradable putty that cures at physiological temperatures, said kit comprising:

A. a pliant taffy, said taffy comprising
  (1) poly-(propylene fumarate),
  (2) vinyl pyrrolidone,
  (3) a filler; and
B. an initiator solution, said solution comprising
  (1) a free radical initiator dissolved in
  (2) vinyl pyrrolidone, whereupon mixing said taffy and said initiator solution produces the putty.

* * * * *